United States Patent
Hirano et al.

(10) Patent No.: US 6,627,740 B2
(45) Date of Patent: Sep. 30, 2003

(54) MONOCLONAL ANTIBODY WHICH BINDS TO A POLYPEPTIDE HAVING PRE-B CELL GROWTH SUPPORTING ABILITY

(75) Inventors: Toshio Hirano, 7-6, Anryu 2-Chome, Suminoe-ku, Osaka-shi, Osaka-fu 559 (JP); Tsuneyasu Kaisho, Hyogo-ken (JP)

(73) Assignee: Toshio Hirano, Osaka (JP)

( * ) Notice: Subject to any disclaimer, the term of this patent is extended or adjusted under 35 U.S.C. 154(b) by 0 days.

(21) Appl. No.: 09/935,720

(22) Filed: Aug. 24, 2001

(65) Prior Publication Data

US 2002/0156260 A1 Oct. 24, 2002

Related U.S. Application Data (62) Division of application No. 09/517,739, filed on Mar. 3, 2000, now Pat. No. 6,307,023, which is a continuation of application No. 08/997,252, filed on Dec. 23, 1997, now Pat. No. 6,232,453, which is a continuation of application No. 08/537,942, filed as application No. PCT/JP94/00819 on May 20, 1994, now Pat. No. 5,753,464.

(30) Foreign Application Priority Data

May 21, 1993 (JP) .............................. 5-141178

(51) Int. Cl.$^7$ .......................... C07K 16/28; C12N 5/12
(52) U.S. Cl. ................ 530/388.22; 530/387.1; 530/387.5; 530/387.9; 530/388.1; 530/388.2; 530/388.24; 435/326; 435/329; 435/331; 435/332; 435/334; 435/343; 435/346
(58) Field of Search ................ 530/388.24, 387.1, 530/387.5, 387.9, 388.1, 388.2, 388.22, 350

(56) References Cited

U.S. PATENT DOCUMENTS

| | | |
|---|---|---|
| 4,965,195 A | 10/1990 | Namen et al. |
| 5,552,303 A | 9/1996 | Grabstein et al. |
| 5,753,464 A | 5/1998 | Hirano et al. |
| 6,232,453 B1 | 5/2001 | Hirano et al. |

FOREIGN PATENT DOCUMENTS

| | | |
|---|---|---|
| EP | 0 314 415 | 5/1989 |

OTHER PUBLICATIONS

Coleman et al. (Research in Immunology, 1994; 145(1): 33–36).*
Abaza et al. (Journal of Protein Chemistry, vol. 11, No. 5, 1992, pp. 433–444).*
Lederman et al. (Molecular Immunology 28: 1171–1181, 1991).*
Ngo et al.; in The Protein Folding Problem and Tertiary Structure Prediction, 1994, Merz et al., (ed.), Birkhauser, Boston, MA, pp. 433 and 492–495.*
Mikayama et al. (PNAS, 1993. 90: 10056–10060).*
Li et al. (PNAS 77: 3211–3214, 1980).*
Lemione et al., "Autocrine Production of Pre–B Cell Stimulating Activity by a Variety of Transformed Murine Pre–B Cell Lines", *Cancer Research,* vol. 48, pp. 6438–6443, Nov. 15, 1988.
Burns, "The Science of Genetics an Introduction to Heredity," 4$^{th}$ Edition, p. 220, 1980. Macmillian Publishing Co., Inc, New York.
Kroczek, "Southern and Northern Analysis," *Journal of Chromatography,* vol. 618, pp. 133–145, 1993.

* cited by examiner

*Primary Examiner*—Phillip Gambel
*Assistant Examiner*—Jessica H. Roark
(74) *Attorney, Agent, or Firm*—Oblon, Spivak, McClelland, Maier & Neustadt, P.C.

(57) ABSTRACT

The present invention provides a monoclonal antibody which binds to a polypeptide as set forth in SEQ ID NO: 1 as described herein.

2 Claims, 2 Drawing Sheets

MONOCLONOL ANTIBODY WHICH BINDS TO A POLYPEPTIDE HAVING PRE-B CELL GROWTH SUPPORTING ABILITY

This application is a divisional of U.S. application Ser. No. 09/517,739, filed on Mar. 3, 2000, now U.S. Pat No. 6,307,023; which is a Continuation of U.S. application Ser. No. 08/997,252, filed Dec. 23, 1997, now U.S. Pat. No. 6,232,453, issued May 15, 2001; which is a Continuation of U.S. application Ser. No. 08/537,942, filed Nov. 21, 1995, now U.S. Pat. No. 5,753,464, issued May 19, 1998; which is a 371 of PCT/JP94/00819, filed May 20, 1994.

BACKGROUND OF THE INVENTION

1. Field of the Invention

This invention relates to a gene and an adhesion molecule encoded by said gene, and in particular, relates to a gene encoding a polypeptide having pre-B cell growth-supporting ability, a vector containing said gene, transformants such as microorganisms or cells transformed by said vector and a method for producing the adhesion molecule having pre-B cell growth-supporting ability by using said gene.

The gene of the present invention encodes a novel adhesion molecule enhancing pre-B cell growth-supporting ability on the surface of bone marrow cells and synovial cells derived from patients with rheumatoid arthritis (RA) or multiple myeloma (MM). In the present invention, a homogeneous and purified adhesion molecule having pre-B cell growth-supporting ability can be produced in large quantities by transforming appropriate host cells with a suitable vector in which the gene of the present invention is inserted. Thus, according to the present invention, it becomes possible to identify multiple myeloma (MM) and rheumatoid arthritis (RA), and also prepare reagents for the clinical diagnosis thereof.

2. Description of the Prior Art

It has been reported that abnormalities of bone marrow cells are actually involved in the pathogenesis of B cell malignancies and autoimmune disease [Annu. Rev. Immunol., 9:243 (1991)].

Namely, multiple myeloma (MM) is a tumor which develops depending on microenvironment in the bone marrow and also a monoclonal plasmacytic tumor characterized by restricted growth in the bone marrow, and several studies have suggested that the oncogenic transformation of multiple myeloma (MM) occurred during the process of the differentiation and proliferation of early B cell development (pre-B cell) which is dependent on bone marrow stromal cells [J. Exp. Med., 150: 792 (1979), and Cancer Genet. Cytogenet, 17:13 (1985)].

Furthermore, the fact has been reported that bone marrow stromal cells were demonstrated to induce the growth of the precursor cells of multiple myeloma (MM) circulating in the peripheral blood of patients with multiple myeloma (MM) [Blood, 77:2688 (1991)].

Therefore, it is probable that bone marrow stromal cells provide stimulatory signals essential for the generation of multiple myeloma (MM).

In this regard, it has been known that the abnormal production of IL-6 may play a role in pathogenesis of rheumatoid arthritis (RA) [Eur. J. Immunol., 18:1797 (1988), and Clin. Immunol. Immunopathol., 62:S60 (1992)]. Besides, according to the results taking several murine autoimmune models into consideration reported in Eur. J. Immunol., 20:723 (1990) and Eur. J. Immunol., 21:63 (1991), it is suggested that the bone marrow derived from patients with rheumatoid arthritis (RA) is probably affected.

Namely, also in rheumatoid arthritis (RA), it is suggested that polyclonal B cell activation is probably caused by the bone marrow adjacent to an affected arthrosis.

The present inventors have engaged in extensive studies with a view to investigate the function of the bone marrow microenvironments in disorders causing abnormalities of B cells, and have reported that the pre-B cell growth-supporting ability of BM stromal cells derived from patients with RA or MM is enhanced in comparison with that of healthy donor-derived BM stromal cells, and that the direct cell-to-cell interaction of pre-B cells and stromal cells might play essential roles in this supporting ability. At the same time, the present inventors have obtained bone marrow specimens derived from patients with MM and RA after informed consent, and established novel stromal cell lines (RASV5-5, MMSV3-3) containing a molecule enhancing the growth of pre-B cells, on the basis of the speculation that there should be a surface molecule enhancing the growth of pre-B cells on the bone marrow stromal cells derived from patients with RA and MM. It has been suggested that the pre-B cell growth-supporting activity of these stromal cell lines is most likely caused by unknown adhesion molecules different from known Stem cell factors (SCF), ICAM-1, CD44, VCAM-1, LFA-1α, LFA-1β, NCAM and ELAM-1 [J. Immunol., 149:4088 (1992)].

Therefore, the present inventors have prepared for a monoclonal antibody using the BM stromal cell line RASV5-5 having enhanced pre-B cell growth-supporting ability derived from patients with RA as an antigen for immunization, and obtained a monoclonal antibody RF3 responding to BM stromal cell lines derived from patients with RA and MM, and not responding to a stromal cell line NFSV1-1 derived from the human bone marrow having no pre-B cell growth-supporting ability.

Further, the present inventors have found that a monoclonal antibody yielded by the hybridoma SG2, which obtained from the immunized cell line SynSV6-14 of the synovial cell derived from patients with RA, responds to BM stromal cell line RASV5-5 derived from patients with RA, and does not respond to the stromal cell line NFSV1-1 derived from the human bone marrow having no pre-B cell growth-supporting ability.

SUMMARY OF THE INVENTION

This invention is directed to a gene and an adhesion molecule encoded by said gene, and in particular, relates to a gene encoding a polypeptide having pre-B cell growth-supporting ability, a vector containing said gene, transformants such as microorganisms or cells transformed by said vector and a method for producing the adhesion molecule having pre-B cell growth-supporting ability by using said gene.

The present invention provides a gene encoding the polypeptide having human pre-B cell growth-supporting ability.

The present invention also provides a recombinant vector containing the gene encoding the polypeptide having human pre-B cell growth-supporting ability.

The present invention further provides a procaryotic or eucaryotic host cell transformed by the recombinant vector containing the gene encoding the polypeptide having human pre-B cell growth-supporting ability.

Furthermore, the present invention provides a method for producing the polypeptide having human pre-B cell growth-supporting ability characterized by culturing a transformant such as microorganisms or cells transformed by the recombinant vector containing the gene encoding the polypeptide having human pre-B cell growth-supporting ability.

The gene of the present invention encodes a novel adhesion molecule enhancing pre-B cell growth-supporting ability on the surface of bone marrow cells and synovial cells derived from patients with rheumatoid arthritis (RA) or multiple myeloma (MM). In the present invention, a homogeneous and purified adhesion molecule having pre-B cell growth-supporting ability can be produced in large quantities by transforming appropriate host cells with a suitable vector in which the gene of the present invention is inserted. Thus, according to the present invention, it becomes possible to identify multiple myeloma (MM) and rheumatoid arthritis (RA), and also prepare reagents for the clinical diagnosis thereof.

DETAILED DESCRIPTION OF THE INVENTION

Since it is probable that the expression of a novel adhesion molecule having pre-B cell growth-supporting ability recognized by the above-mentioned hybridomas is probably correlate with the degree of the disorders of patients with RA and MM, it becomes to be important problems that investigating the properties of the membrane protein, and securing thereof in large quantities capable of being utilized for diagnosis, remedies and studies of RA and MM. Therefore, investigating the structures of genes of the adhesion molecule and establishing the mass production technique of the adhesion molecule by using recombination DNA technique have been desired.

That is, the present invention is directed to provide a gene encoding a polypeptide having pre-B cell growth-supporting ability, a vector containing said gene, transformants such as microorganisms or cells transformed by said vector and a method for producing the adhesion molecule having pre-B cell growth-supporting ability by using said gene.

Under such circumstances, the present inventors have prepared cDNAs library from mRNA prepared from cells expressing an adhesion molecule, and then inserted these cDNAs into an expression vector to obtain transformants such as microorganisms or cells transformed by the expression vector. Subsequently, the present inventors have succeeded in cloning the genes of a novel adhesion molecule having pre-B cell growth-supporting ability by repeating the steps, which consist of selecting transformants responding strongly to a monoclonal antibody produced by said hybridomas, further sorting cDNAs used for the preparation thereof and inserting them into the expression vector again, selecting transformants responding strongly to said antibody, and further sorting cDNAs used for the preparation thereof. In addition, the present inventors have found that the novel adhesion molecule can be produced in large quantities, by obtaining a transformant by inserting the gene into a proper vector, and then culturing it.

Therefore, the present invention provides a gene encoding the polypeptide having human pre-B cell growth-supporting ability.

The present invention also provides a recombinant vector containing the gene encoding the polypeptide having human pre-B cell growth-supporting ability.

The present invention further provides a procaryotic or eucaryotic host cell transformed by the recombinant vector containing the gene encoding the polypeptide having human pre-B cell growth-supporting ability.

Furthermore, the present invention provides a method for producing the polypeptide having human pre-B cell growth-supporting ability characterized by culturing a transformant such as microorganisms or cells transformed by the recombinant vector containing the gene encoding the polypeptide having human pre-B cell growth-supporting ability.

Subsequently, the present invention will be described in detail.

The gene of the present invention is obtained, for example, by preparing mRNA from a cell expressing an adhesion molecule having human pre-B cell growth-supporting ability, and then converting it into a double-stranded cDNA according to a known method. As a cell used for preparing the mRNA can be mentioned cell lines RASV5-5 and SynSV6-14 used as immune sources of hybridomas RF3 and SG2, but it is not limited to these cell lines and therefore any type of cells expressing the adhesion molecule having human pre-B cell growth-supporting ability may be used. As one example thereof can be mentioned various stromal cell lines disclosed in J. Immunol., 149:4088 (1992). Incidentally, SynSV1-4 was used in the present invention.

For the preparation of the total RNA for obtaining mRNA can be employed a method for obtaining the total RNA which consists of performing cesium chloride density-gradient centrifugation after a guanidine thiocyanate treatment [Chirgwin et al., Biochemistry, 18:5294 (1979)], a method which consists of performing a surfactant treatment and a phenol treatment in the presence of the ribonuclease inhibitor of a vanadium complex [Berger & Birkenmeier, Biochemistry, 18:5143 (1979)], and other known methods.

The preparation of mRNA from the total RNA, can be accomplished by recovering poly(A) +RNA from the total RNA according to, for example, affinity column chromatography using Sephalose or cellulose, or a batch method. Besides, poly(A) +RNA can be further purified according to sucrose density-gradient centrifugation. In addition, there can be mentioned a method for obtaining poly(A) +RNA directly without preparing RNA or a convenient method using a commercially available kit.

In order to obtain a double-stranded cDNA from the thus obtained mRNA, for example, a DNA (cDNA) complementary to mRNA is synthesized by using mRNA as a template, and using an oligo (dT) complementary to a poly-A-chain sited at the 3' end as a primer, and the treating it with reverse transcriptase.

The double-stranded cDNA can be also obtained by degrading mRNA according to an alkaline treatment, subjecting the obtained single-stranded cDNA as a template to a treatment with reverse transcriptase or DNA polymerase (e.g., Klenow fragment), and then treating it with S1 nuclease, or treating it directly with RNase and DNA polymerase [Maniatis et al., Molecular Cloning, Cold Spring Harbor Laboratory (1982) and Gubler & Hoffman, Gene, 25:263 (1983)]. Nowadays, convenient kits have been on the market, and a double-stranded cDNA can be obtained by using them.

The cDNAs library can be obtained by inserting the thus obtained cDNA into a proper vector, for example, an EK-type plasmid vector such as pBR322 and pSC101, and a phage vector such as λgt10, and then transforming Escherichia coli with said vector (e.g., X1776, HB101, DH1, DH5) or the like (refer, for example, to "Molecular Cloning" above).

On the other hand, host cells of other procaryotes and eucaryotes can be transformed by using a suitable expression vector in which the double-stranded cDNA obtained according to the above-mentioned method is inserted.

The ligation of the double-stranded cDNA to the vector can be performed by adding a proper chemically-synthesized DNA adapter thereto, and subjecting it with a vector DNA cleavaged by means of a restriction enzyme to a treatment with T4 phage DNA ligase in the presence of ATP.

The expression vector of the present invention contains a replicative origin, a selective marker, a promoter located in upstream region of a gene to be expressed, an RNA splice site and a polyadenylated signal.

As a gene expression promoter in a mammal cell may be used virus promoters such as retrovirus, polyoma virus, adenovirus and simian virus (SV) 40, and promoters derived from cells such as human polypeptide chain elongation factor 1α (HEF-1α). For example, in case of using a promoter of SV40, it can be performed easily according to a method of Mulligan et al. [Nature, 277:108 (1979)].

As a replicative origin can be used those derived from SV40 polyoma virus, adenovirus and bovine papilloma virus (BPV), and as a selective marker can be used a phosphotransferase APH (3') II or I (neo) gene, a thymidine kinase (TK) gene, an *Escherichia coli* xanthine-guanine phosphoribosyl transferase (Ecogpt) gene and a dihydrofolate reductase (DHFR) gene.

In order to express the desired gene using a procaryotic cell as a host cell, the host cell is transformed with a replicon derived from species capable of being fitted as hosts, namely, a plasmid vector containing a replicative origin and a regulation sequence. A vector which has a marker gene capable of imparting the selectivity of a phenotype to transformed cells is preferable. For example, in case of using *Escherichia coli* as a host cell, it can be transformed using pBR322, a vector originated from the host cell [Boliver et al., Gene, 2:95 (1975)]. The pBR322 contains an ampicillin resistant gene and a tetracycline resistant gene, and therefore transformants can be identified by utilizing either of these resistant properties. As a promoter needed for the gene expression of a procaryotic host cell can be mentioned a promoter of a β-lactamase gene [Chang et al., Nature, 275:615 (1978)], a lactose promoter [Goeddle et al., Nature, 281:544 (1979)], a tryptophan promoter [Goeddle et al., Nucleic Acid Res., 8:4057 (1980)], a tac promoter and the like.

As procaryotic host cells of hosts to be used in the expression system of the present invention can be mentioned *Escherichia coli, Bacillus subtilis, Bacillus thermophilus* and the like.

In addition, as eucaryotic host cells can be mentioned eucaryotic microorganisms such as *Saccharomyces cerevisiae*, and cells derived from mammals such as a COS cell, a Chinese hamster ovary (CHO) cell, a C127 cell, a 3T3 cell, a Hela cell, a BHK cell, a namalwa cell and a human fetal renal cell (293 cell).

Incidentally, the culture of the transformants of the present invention may be performed by selecting culture conditions suitable for host cells appropriately, The isolation of a cDNA encoding an adhesion molecule having pre-B cell growth-supporting ability can be performed, for example, by using pre-B cell growth-supporting ability as an index or according to a method such as direct expression cloning using an antibody. The measurement of pre-B cell growth-supporting ability can be performed by using a murine pre-B cell line DW34 [Eur. J. Immunol., 18:1767 (1988)].

That is, a cell expressing the adhesion molecule having pre-B cell growth-supporting ability is cultured until it becomes subconfluent on 24-well plates (preferable density being about 50%) and a proper amount of radiation is irradiated thereupon, DW34 of 1 to $2 \times 10^3$ per well is added thereto, and cultured in RPMI-1640 medium containing 10% FCS under the condition of 5% $CO_2$ at 37° C. for about 4 to 6 days. The degree of the enhancement of the growth-supporting ability can be found by examining the number of living cells of DW34 in each well according to trypan blue dye exclusion.

In the present invention, the desired gene could be cloned by repeating the steps, which consists of selecting a transformant expressing an adhesion molecule according to an FACScan using monoclonal antibodies RF3 and SG2 recognizing the adhesion molecule having pre-B cell growth-supporting ability, preparing a transformant again by sorting the plasmid DNA used for the preparation of the transformant, and then screening the transformant according to flow cytometry.

Namely, a transduced transformant (293T cell) was cultured on well plates and removed from the plates with PBS containing 0.02% EDTA, and after the cell was washed with an FACS buffer solution composed of PBS containing 2% FCS and 0.02% $NaN_3$, it was reacted with RF3 and SG2 as primary antibodies. Subsequently, after the unreacted primary antibodies were removed by washing it with an FACS buffer solution, it was further reacted with a secondary antibody, an FITC-labeled antibody (FITC-labeled anti-mouse goat Ig antibody), dead cells were stained with propidium iodide, and viable cells were analyzed by an FACScan to select transformants responding strongly to RF3 and SG2.

Further, the complete length of cDNA (63-BOS) encoding a membrane protein polypeptide having novel pre-B cell growth-supporting ability shown in sequence No. (SEQ ID NO) 2 of the sequence table (SEQUENCE TABLE) could be obtained by repeating the steps, which consists of treating *Escherichia coli* (DH5) containing the cDNA used for the preparation of transformants responding to antibodies with alkali to select a group of plasmids containing the desired gene, subdividing the group of plasmids into some groups of plasmids, transducing them into 293T cells again, and then selecting transformants according to FACScan analysis using the above-mentioned monoclonal antibodies RF3 and SG2.

Incidentally, the Escherichia coli DH5α strain containing pBst-1 with the cDNA inserted into the XbaI cleavage sites of a pUC19 vector was deposited at National Institute of Bioscience & Human-Technology, Agency of Industrial Science and Technology in Japan (Address: 1–3, Higashi 1-chome, Tsukuba-shi, Ibaraki 305, JAPAN), which is international depositary authority according to Budapest Treaty on the international recognition of the deposit of microorganisms for the purpose of patent procedure, on May 19, 1993, under the name of *Escherichia Coli* DH5 α (pBst-1) with accession No. FERM BP-4305.

Generally, the genes of eucaryotes are thought to show polymorphism as known according to human interferon genes [e.g., Nishi et al., J. Biochem., 97: 153 (1985)], and in some cases at least one amino acid is substituted according to this polymorphism, and in other cases amino acids do not change at all though there are changes in the DNA sequence.

Further, it is probable that some polypeptides having at least one more or less amino acid than the amino acid sequence shown in sequence No. 1 of the sequence table, or some polypeptides substituted with at least one amino acid may have also pre-B cell growth-supporting ability. Actually, for example, it has been already known that the polypeptide obtained from a human interleukin (IL-2) gene, in which a DNA sequence corresponding to cysteine is converted to a sequence corresponding to serine, holds also an IL-2 activity [Wang et al., Science, 224:1431 (1984)].

Moreover, a known protein gene and a gene shown in sequence No. 2 of the sequence table can be ligated by means of a proper restriction enzyme or adaptor to yield a polypeptide bound to the known protein. As this know protein gene can be mentioned immunoglobulin, and it may be bound to an Fc portion of it using the gene shown in sequence No. 2 of the sequence table instead of the variable region site of it [(Zettlmeissl et al., DNA AND CELL BIOLOGY, 9:347–353 (1990)].

Furthermore, in case of expressing a polypeptide in eucaryotic cells, glycosylation occurs in many cases, and the glycosylation can be regulated according to the conversion of at least one amino acid; in this case, too, they may have pre-B cell growth-supporting ability.

Therefore, even the genes in which the site encoding a polypeptide having pre-B cell growth-supporting ability are modified artificially can be included in the present invention so far as the polypeptides obtained from the genes have pre-B cell growth-supporting ability.

Moreover, genes to be hybridized with genes shown in sequence No. 2 of the sequence table are also included in the present invention so far as the polypeptides expressed from the genes have pre-B cell growth-supporting ability. Hybridization may be carried out according to employing ordinary hybridization conditions (for example, refer to the above-mentioned "Molecular Cloning").

A homogeneous and purified soluble adhesion molecule can be obtained by culturing a transformant such as microorganisms or cells transformed with a gene encoding a polypeptide having pre-B cell growth-supporting supporting ability to be desired, solubilizing the yielded polypeptide with proper detergent, subjecting the resultant polypeptide to separation and purification. Examples of the detergent include Nonidet P-40 (NP-40), Sodium Dodecyl Sulphate (SDS), Triton X-100, Tween 20 and the like.

In addition, the soluble adhesion molecules can be also prepared according to gene engineering. Namely, since the portion from the 272nd Gln to the 290th Leu in sequence No. 1 of the sequence table is a region with high hydrophobic properties, a gene having a termination codon at a position before the 272nd position can be prepared by employing a PCR-mutagenesis method [M. Kamman et al., Nucl. Acids Res., 15:5404 (1989)].

Also describing in detail, the gene of the deposited pBst-1 is amplified according to the PCR-mutagenesis method employing two primers AAC CTC CAG AAG GAA AA (corresponding to the 185th to the 190th of sequence No. 1 of the sequence table) and ACC CAA GCT TTC TAG ATC AAT AAA GAC TTG GGG CTT (corresponding to the 264th to the 269th of sequence No. 1 of the sequence table + a termination codon + HindIII and the XbaI restriction site). The desired gene is purified using low melting point agarose and the like, and cleaved to fragments with BglII and HindIII. After the obtained BglII-HindIII fragment is inserted into the pBst-1 which was digested with the same restriction enzyme, it is digested with EcoRI and HindIII, and treated with a Klenow fragment to make a flush end. The DNA fragment is ligated with pEF-BOS which is digested with BstXI, and treated with the Klenow fragment, and a proper host cell is transformed with it to yield a soluble adhesion molecule.

As a means of separation and purification of the molecule, a method to be used in the case of ordinary protein can be employed; for example, the polypeptide of the present invention can be separated and purified properly by selecting and combining various types of chromatography such as affinity chromatography using the above-mentioned monoclonal antibodies, ultrafiltration, salting out, dialysis and the like.

In order to demonstrate the subject invention, a gene encoding the adhesion molecule having pre-B cell growth-supporting ability, a recombinant vector having said gene, transformants containing it, the desired protein obtained by culturing the transformants and methods for producing them, will be described in detail according to Referential Examples and Examples hereinafter, although the present invention is not limited to these Examples.

REFERENTIAL EXAMPLES

Referential Example 1

Establishment of Stromal Cell Lines Derived from Patients with Rhematoid Arthritis (RA) and Healthy-donors That can Support Pre-B Cell Growth.

Mononuclear cell fractions of the bone marrow (BM) derived from patients with rhematoid arthritis (RA) and healthy donors were obtained according to Ficoll-Hypaque density-gradient centrifugation, and cultured in RPMI-1640 culture medium containing 10% fetal calf serum (FCS), 50 $\mu$M 2-mercaptoethanol and antibiotics at 37° C. for several weeks. Washing thereof was repeated to remove non-adhesive cells, and the remaining adhesive cells were electroporated with a pAct-SVT plasmid containing an SV40 large T antigen cDNA and a chicks β-actin promoter [BBRC, 186:129–134 (1992)] by means of a Gene Pulser (manufactured by BioLad).

The above cells and plasmids were incubated in water for 15 minutes, subjected to electroporation at 250 V and at an electrostatic capacity of 250 $\mu$F, further incubated on ice for 10 minutes and cultured in a 10-centimeter dish. Colonies including adhesive cells growing thereupon were harvested with a small piece of filter paper to obtain BM stromal cell lines derived from patients with rheumatoid arthritis (RA) and healthy donors (RASV5-5 and NFSV1-1) [J. Immunol., 149: 4088 (1992)].

Referential Example 2

Establishment of a Synovial Cell Line Derived from Patients with Rhematoid Arthritis (RA) Having Pre-B Cell Growth-Supporting Ability Onto the synovial cells derived from patients with rhematoid arthritis (RA) were electroporated with a pAct-SVT plasmid containing an SV40 large T antigen cDNA and a chicks β-actin promoter [BBRC, 186:129–134 (1992)] by means of a Gene Pulser (manufactured by BioLad). Namely, 0.8 ml of an aliquot of the synovial cell of 1×10⁷ cells/ml derived from patients with RA in PBS were mixed with 10 μg of the plasmid, and the mixture was incubated on ice for 10 minutes, subjected to electroporation under the conditions of 250 V and at an electrostatic capacity of 250 μF, further incubated on ice for 10 minutes, suspended in RPMI-1640 medium (manufactured by GIBCO) containing 10% FCS (manufactured by Bioproducts), and cultured in a 10-centimeter culture dish. The culture medium was changed every three days, and colonies of well-grown adhesive cells were harvested about 2 weeks later with a small piece of filter paper impregnated with trypsin to obtain synovial cell lines derived from RA (SynSV1-4 and SynSV6-14).

Referential Example 3

Preparation of Monoclonal Antibodies
1) Antigens and Immunization

The stromal cell line RASV5-5 and the synovial cell line SynSV6-14 derived from patients with RA having high pre-B cell growth-supporting ability obtained in the above Referential Examples 1 and 2 was used as antigens for immunization. Using RPMI-1640 medium (manufactured by GIBCO) containing 10% fetal calf serum (FCS, manufactured by Bioproducts) and 50 μM 2-mercaptoethanol as a medium, the cell lines were subcultured in an incubator containing 5% $CO_2$, at 37° C.

The cells were treated with 0.02% EDTA and PBS, and recovered from a culture flask of the incubator according to pipetting. The cells were suspended into the RPMI 1640 medium at a rate of about $1 \times 10^7$ cells/ml, and immunized to a BALB/C mouse (4-week old, female, manufactured by L. S. C of Japan). In the initial immunization, about $1 \times 10^7$/ml cells were injected into the abdominal cavity of the mouse, and 2 to 3 weeks later, $1 \times 10^7$/ml cells were injected as additional immunization. Further, at intervals of 2 to 3 weeks, about $1 \times 10^7$/ml cells were injected 2 to 3 times as additional immunization, and 3 days later the final immunization, the mouse was sacrificed and the spleen was obtained for fusion.

2) Cell Fusion

After the spleen extirpated from one mouse was cut to pieces, isolated spleen cells were centrifuged, suspended into RPMI-1640 medium (manufactured by GIBCO), and washed sufficiently. On the other hand, $1 \times 10^7$ cells obtained by culturing a mouse-myeloma cell line P3X63Ag8.653 [J. Immunol., 123:1548 (1979)] in DMEM (manufactured by GIBCO) medium containing 10% fetal calf serum (FCS, manufactured by FILTRON) were washed in the above DMEM medium similarly, and were introduced into a centrifugal tube with $1 \times 10^8$ said spleen cells and mixed, and then were subjected to cell-fusion with polyethylene glycol 1500 (manufactured by Boehringer) according to ordinary procedure [Clin. Exp. Immunol., 42:458–462 (1980)].

The obtained fused cells were introduced into 96-well plates in DMEM medium containing 10% FCS, and cultured in an incubator containing 5% $CO_2$, at 37° C.

From the following day, the medium was replaced with HAT selective medium (complete RPMI-1640 medium containing $1.0 \times 10^{-4}$ M hypoxanthine, $4.0 \times 10^{-7}$ aminopterin and $1.6 \times 10^{-5}$ M thymidine having 10% FCS and 50 μM 2-mercaptoethanol added therein) slowly, and the culture was continued. After culture was initiated, half of the supernatant was replaced with new HAT medium 2 times per week, and the culture was continued to maintain proliferation.

The thus obtained fused cells were cloned according to limiting dilution analysis.

That is, using the antibodies in the culture supernatant obtained by culturing the above fused cells, respondency with the antigens were examined, and clones having strong respondency with the antigens alone were obtained according to ordinary procedure employing a limiting dilution analysis.

So as to perform the formation of clones, the above hybridoma and the spleen cells of a BALB/C mouse were prepared in prescribed amounts, inoculated onto 96-well plates at a rate of 1 to 10 hybridoma(s) per well, and cultured in an incubator containing 5% $CO_2$, at 37° C. The operation of cloning hybridomas grown was repeated in the same manner according to ordinary limiting dilution analysis until they became a single clone theoretically. Clones yielding the desired antibody were screened using the above antigens.

Thus, 2 kinds of hybridomas (RF3, SG2) yielding antibodies that respond to RASV5-5 but not respond to the stromal cell line NFSV1-1 derived from the bone marrow of healthy donors having no pre-B cell growth-supporting ability were separated. The antibodies yielded by these hybridomas were IgG2a and IgG2a.

Incidentally, said hybridomas yielding the above monoclonal antibodies RF3 and SG2 are novel fused cells which produced with the spleen cells of a BALB/C mouse and mouse myeloma P3X63Ag8.653 as parent cells, and were deposited at National Institute of Bioscience & Human-Technology, Agency of Industrial Science and Technology in Japan (Address: 1–3, Higashi 1-chome, Tsukuba-shi, Ibaraki 305, JAPAN), which is international depositary authority according to Budapest Treaty on the international recognition of the deposit of microorganisms for the purpose of patent procedure, on Apr. 28, 1993, under the names of Mouse—Mouse hybridoma RF3 with accession No. of FERM BP-4656, and Mouse—Mouse hybridoma SG2 with accession No. of FERM BP-4657.

3) Screening

The screening of fused cells (hybridomas) was performed according to indirect fluorescent antibody technique, flow cytometry analysis by means of a flow cytometer.

The screening of clones yielding the objective antibody was performed using a) RASV5-5 (antigen for immunization) and b) the stromal cell line NFSV1-1 derived from the bone marrow of healthy donors as target cells. Namely, after immunizing the BM stromal cell line (RASV5-5) derived from patients with RA having high pre-B cell growth-supporting ability to a BALB/C mouse, the screening of monoclonal antibodies that respond to RASV5-5 but not respond to the BM stromal cell line (NFSV1-1) derived from healthy donors having no pre-B cell growth-supporting ability was performed as follows. The first screening was performed using RASV5-5, a cell to be subjected to reaction, as an antigen for immunization. First of all, culture supernatant responding to RASV5-5 were selected with a view to selecting fused cell clones responding to said RASV5-5, and then a primary screening was performed.

Namely, cells suspended in a reaction buffer (PBS containing 2% FCS and 0.02% $NaN_3$) were suspended into 20 μl of a hybridoma culture supernatant (about $5 \times 10^5$/20 μl), and reacted at 4° C. for 20 minutes.

They were washed with the above buffer twice, and the FITC-labeled anti-mouse goat Ig antibody (manufactured by Cappel) was added therein, and the mixture was incubated for 20 minutes. After the reaction product was washed three times, it was analyzed by means of a flow cytometer (FACScan, manufactured by Becton Dickinson).

Subsequently, the BM stromal cell line NFSV1-1 derived from healthy donors was used as a cell to be subjected to reaction, and analyzed by means of a flow cytometer as above. Two kinds of cells were obtained as hybridomas yielding antibodies responding strongly to RASV5-5 according to it.

4) Purification of Antibodies

The fused cells prepared in the above 2) were cultured according to ordinary procedure, and the antibodies yielded in the culture supernatant were purified according to ordinary procedure.

That is, hybridomas were collected from the wells with the highest antibody titer to the above antigen, and one well in which the growth of cells could be recognized was taken out, and the obtained culture cells were expanded into a tissue culture flask under the conditions of 5% $CO_2$ at 37° C., and were grown. The obtained cells were injected into the peritoneal cavity of a BALB/C mouse (6-week old, female, manufactured by S. L. C. of Japan) with pristan dosed. And 10 to 14 days after, the ascites was collected, salted out with 50% ammonium sulfate, dialyzed with PBS and purified with a QAE column. The antibodies were further salted out, and dialyzed sufficiently to obtain a purified product of about 6 mg/ml.

Referential Example 4

Mouse monoclonal antibodies RF3 and SG2 selectively recognizing the BM stromal cell lines derived from patients with RA having pre-B cell growth-supporting ability were found to recognize the same molecule according to the following method.

Namely, after each antibody was biotinated by means of N-hydroxysuccinimide biotin [Antibodies: A Laoratory Manual, E. Harlow e t al., Cold Spring Harbor Laboratory Press (1988)], a cross inhibition test using the BM stromal cell line RASV5-5 derived from patients with RA was performed. The RASV5-5 cell line was suspended in 20 μl of an FACS buffer comprising phosphate-buffered saline (PBS) containing 2% FCS and 0.02% $NaN_3$ in combination of biotinated RF3 and SG2, or biotinated SG2 and RF3, incubated on ice for 20 minutes, washed with an FACS buffer solution twice, and after FITC-labeled streptoavidin was added therein, the resultant product was further incubated on ice for 20 minutes. After it was washed with an FACS buffer solution three times, it was analyzed on a FACScan (manufactured by Becton Dickinson), and cross inhibition was found in any combination. According to the above, it was deemed that mouse monoclonal antibodies RF3 and SG2 recognized the same epitope of the same molecule or the epitope extremely close to it.

EXAMPLE

A detailed description of the examples of the invention is presented below.

Example 1

1. Preparation of a cDNA Library

1) Preparation of Poly (A) +RNA

The preparation of poly (A) +RNA from the synovial cell line SynSV1-4 derived from patients with rhematoid arthritis (RA) was performed using a Fast Track™ mRNA isolation kit version 3.2 (manufactured by Invitrogen).

That is, SynSV1-4 cells for twenty 10-centimeter culture dishes were homogenized, and then the total RNA was prepared according to the procedure attached to the kit. Further, the poly (A) +RNA was purified by means of oligo (T) cellulose attached to the kit according to the procedure attached to the kit.

2) Construction of the cDNA Library

A double-stranded cDNA was synthesized using the above poly (A) +RNA of 5 μg as a material according to the procedure attached to the cDNA synthesis kit, Time Saver™ cDNA synthesis kit (manufactured by Pharmacia), and a BstXI adapter (manufactured by Invitrogen) was ligated thereto by means of a DNA ligation kit (manufactured by Takara Shuzo) according to the procedure attached to the kit. The removal of the free BstXI adapter was performed by means of the Size Sep 400 Spin Column attached to the kit according to the procedure attached to the kit to obtain about 100 μl of an adapter-ligated double-stranded cDNA.

And then, of about 100 μl of the prepared adapter-ligated double-stranded cDNA, 2 μl of it were used in one ligation reaction, and a cDNA library was constructed by ligating it with a pEF-BOS vector [Nuc. Acid Res., 18:5322 (1990)] treated in advance with a restriction enzyme BstXI and alkali phosphatase (manufactured by Takara Shuzo) by means of a DNA ligation kit (manufactured by Takara Shuzo). The constructed cDNA was transformed into the *Escherichia coli* cell strain DH5 (manufactured by Toyobo), and was presumed to be an independent clone with the total size of about $2\times10^5$. 50 pools, each pool comprising 2000 to 4000 clones of transduced *Escherichia coli*, were prepared, and then used in the following tests.

2. Cloning According to Direct Expression Method

1) Trasfection into 293T Cells

The amplification of a cDNA was performed by culturing the above pooled *Escherichia coli* in LB medium containing 50 μg/ml of ampicillin [Molecular Cloning: A Laboratory Manual, Sambrook et al, Cold Spring Harbor Laboratory Press (1989)], and a plasmid DNA was recovered from the *Escherichia coli* according to an alkaline method [Molecular Cloning: A Laboratory Manual, Sambrook et al, Cold Spring Harbor Laboratory Press (1989)]. The degree of the purification of the obtained plasmid DNA was enhanced by repeating ultra-centrifugation according to cesium chloride/ethidium bromide density-gradient centrifugation, and the purified plasmid DNA was transfected to a 293T cell [cell line prepared by transfecting an SV40 large T antigen cDNA into a 293 cell (Transformed primary embryonal kidney, human ATCC CRL 1573)] according to a calcium phosphate method.

Namely, 2 μg of the purified plasmid DNA was dissolved into 100 μl of a buffer solution containing 1 mM of Tris-HCl and 0.1 mM of EDTA, and after 14 μl of 2M $CaCl_2$ were added therein, and the resultant mixture was mixed with a buffer solution composed of 50 mM of HEPES (pH: 7.1), 280 mM of NaCl, and 1.5 mM of sodium phosphate slowly, and then the obtained mixture was incubated at room temperature for 30 minutes and added to the 293T cells in a 24-well plates. The 293T cells were cultured in DMEM (manufactured by GIBCO) medium containing 10% fetal calf serum (FCS, manufactured by Bioproducts) under the conditions of 37° C. and 5% $CO_2$ for 2 days.

2) Analysis According to FACS

The transduced 293T cells were removed from the 24-well plates in PBS containing 0.02% EDTA, and washed with an FACS buffer solution comprising PBS containing 2% FCS and 0.02% $NaN_3$ twice, and then suspended in 20 μl of the FACS buffer solution in the presence of a mixture of 10 μg/ml of RF3 and SG2 as a primary antibody and incubated on ice for 20 minutes. After they were washed with the FACS buffer solution twice, they were further incubated on ice for 15 minutes, using an FITC-labeled anti-mouse goat Ig antibody (manufactured by Cappel) as a secondary antibody. Propidium Iodide (PI) was added therein so that the final concentration of it became 1 µg/ml, and the mixture was further incubated on ice for 5 minutes, washed with the FACS buffer solution three times, and the cells were analyzed with light scattering measurement and viable cells alone were subjected to an FACScan (manufactured by Becton Dickinson).

3) Cloning of the cDNA Library

The plasmid DNAs recovered from *Escherichia coli* of 2000 to 4000 clones as one pool according to alkaline method were transfected to 293T cells according to the above method, and the transfected cells were subjected to screening according to the above FACS analysis. A peak strongly stained with mouse monoclonal antibodies RF3 and SG2 was recognized in the 20th pool of the 293T cells. The plasmid DNA was transduced into *Escherichia coli* DH5α (manufactured by GIBCO BRL) again, and it was inoculated onto LB agar plate containing 50 µg/ml of ampicillin.

And 2000 clones forming colonies were inoculated one by one onto an agar plate with its bottom was divided into a net-like state so that the position of a clone inoculated was recognized at a rate of 100 clones per plate, and two series of the each plate were prepared. 20 pools, each pool comprising 100 clones, were prepared in the same way, and the *Escherichia coli* was cultured in LB medium containing 50 µg/ml of ampicillin. After plasmid DNAs were recovered according to an alkaline method, they were transfected to 293T cells according to a calcium phosphate method, and the transfected cells were subjected to an FACS analysis in the same manner as above. As a result of the FACS analysis, 100 clones of the *Escherichia coli* were isolated one by one from one pool recognized to be positive, and each clone was cultured, and then plasmid DNAs were recovered according to an alkaline method. Each plasmid DNA was transfected to 293T cells according to a calcium phosphate method, and the FACS analysis was performed in the same manner as above to obtain a single positive clone, which was designated as 63-BOS.

The clone was subjected to a sequence reaction using Auto Read sequencing kit (manufactured by Pharmacia) and Auto Cycle sequencing kit (manufactured by Pharmacia) according to the procedure attached to the kits, and the determination of DNA sequence of it was performed by means of an A. L. E.™ DNA sequenator (manufactured by Pharmacia). As a result, it was a novel gene with the full length of 1411 bp (sequence No. 2 of the sequence table) to be presumed to encode a sequence of the 318 amino acid residues from the longest open reading frame.

3. Expression by a BALB3T3 Cell

The novel molecule was transfected into a BALB3T3 cell and the expression in mammalian cells was examined.

Namely, 20 µg of 63-BOS and 2 µg of pSV2neo which has a neomycin resistant gene [P. J. Souethem and P. Berg, J. Mol. Appl. Genet., 1:327 (1982)] were added into 0.8 ml of aliquot of 1×10$^7$ cells/ml, and incubated on ice for 10 minutes, and then subjected to transfection by means of a Gene Pulser (manufactured by BioLad) under the conditions of 250 V and an electrostatic capacity of 250 µF to accomplish transduction simultaneously.

Further, after it was incubated on ice for 10 minutes, the cell was suspended in DMEM medium (manufactured by GIBCO) containing 2 mg/ml of G418 and 10% FCS (manufactured by Bioproducts), and cultured in 24-well plates. The exchange of a culture medium was performed every three days, and about 2 weeks later, a transformed cell BALB3T363S2 responding to the above mouse monoclonal antibody RF3 was obtained from the well forming a single colony of well-grown adhesion cells having neomycin resistance. In addition, as a control cell was obtained a transformed cell BALB3T363S1 not responding to RF3 but having neomycin resistance.

4. Biological Properties of the Novel Molecule

The biological properties of the novel molecule were analyzed using a mouse pre-B cell line DW34 growing dependent on stromal cells with the number of grown cells as an index according to the following method.

Figure 1:
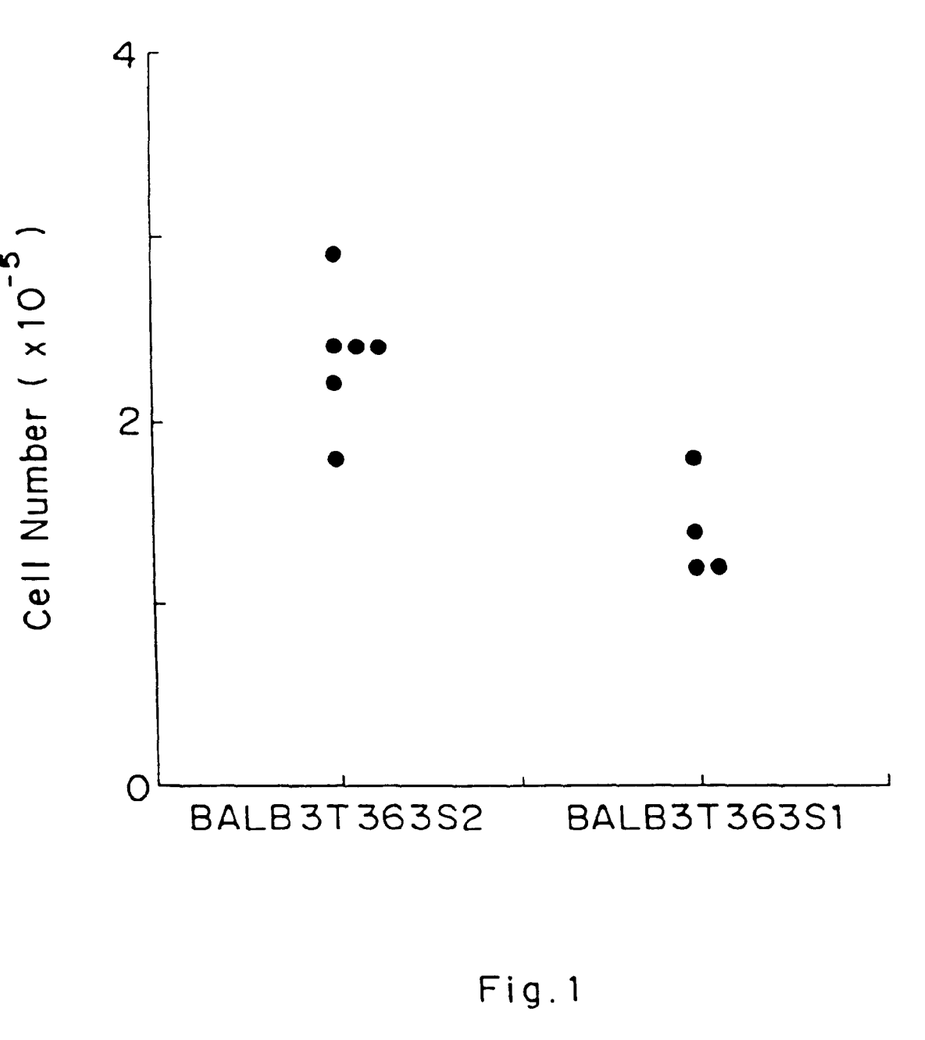
FIG. 1 shows the growth ability of the mouse pre-B cell line DW34 of a novel adhesion molecule obtained in Examples of the present invention.

First of all, the transduced cell BALB3T363S2 and the control cell BALB3T363S1 were cultured in 24-well plates until they became subconfluent, radiation of 30 Gy was irradiated thereupon, DW34 of 2×10$^3$ per well was added therein, and the resultant product was cultured in RPMI-1640 (manufactured by GIBCO) medium containing 10% FCS (manufactured by Bioproducts) under the conditions of 37° C. and 5% $CO_2$ for 4 days. The number of viable cells of DW34 in each well was counted with trypan blue dye exclusion to analyze a growth-supporting ability. As a result, the growth of DW34 was enhanced in the transduced cell BALB3T363S2 in comparison with the control cell BALB3T363S1 as shown in FIG. 1.

5. Physicochemical Properties of the Novel Molecule

1) Recognition of Glycosylphosphatidylinositol (GPI) anchored Protein

The bone marrow stromal cell line RASV5-5 derived from RA or the transduced cell BALB3T363S2 was incubated in PBS containing 1% FCS at 37° C. in the presence or absence of 2 U/ml of phosphatidylinositol specific phospholipase C (PIPLC, manufactured by Funakoshi) for 1 to 2 hours, washed with the above FACS buffer solution twice, and then incubated on ice in the presence of RF3 for 20 minutes. After it was washed with the FACS buffer solution twice, it was further incubated with the FACS buffer solution containing an FITC-labeled anti-mouse goat Ig antibody (manufactured by Cappel) on ice for 20 minutes, and washed with the FACS buffer solution three times, and then subjected to an FACScan (manufactured by Becton Dickinson).

As a control test, CD29 (VLA β1, manufactured by Immunotech) was used in RASV5-5, and R25 in BALB3T363S2 [J. Immunol., 148:989–995 (1992)] as a primary antibody, and as a secondary antibody, the same antibody as the above was used. As a result, though any change of fluorescent strength was not recognized in CD29 and R25, the decrease of fluorescent strength was recognized in those using an RF3 antibody. It is probable that the novel molecule may be bound to a cell membrane through GPI according to the result.

2) Analysis of the N Terminal

Figure 2:
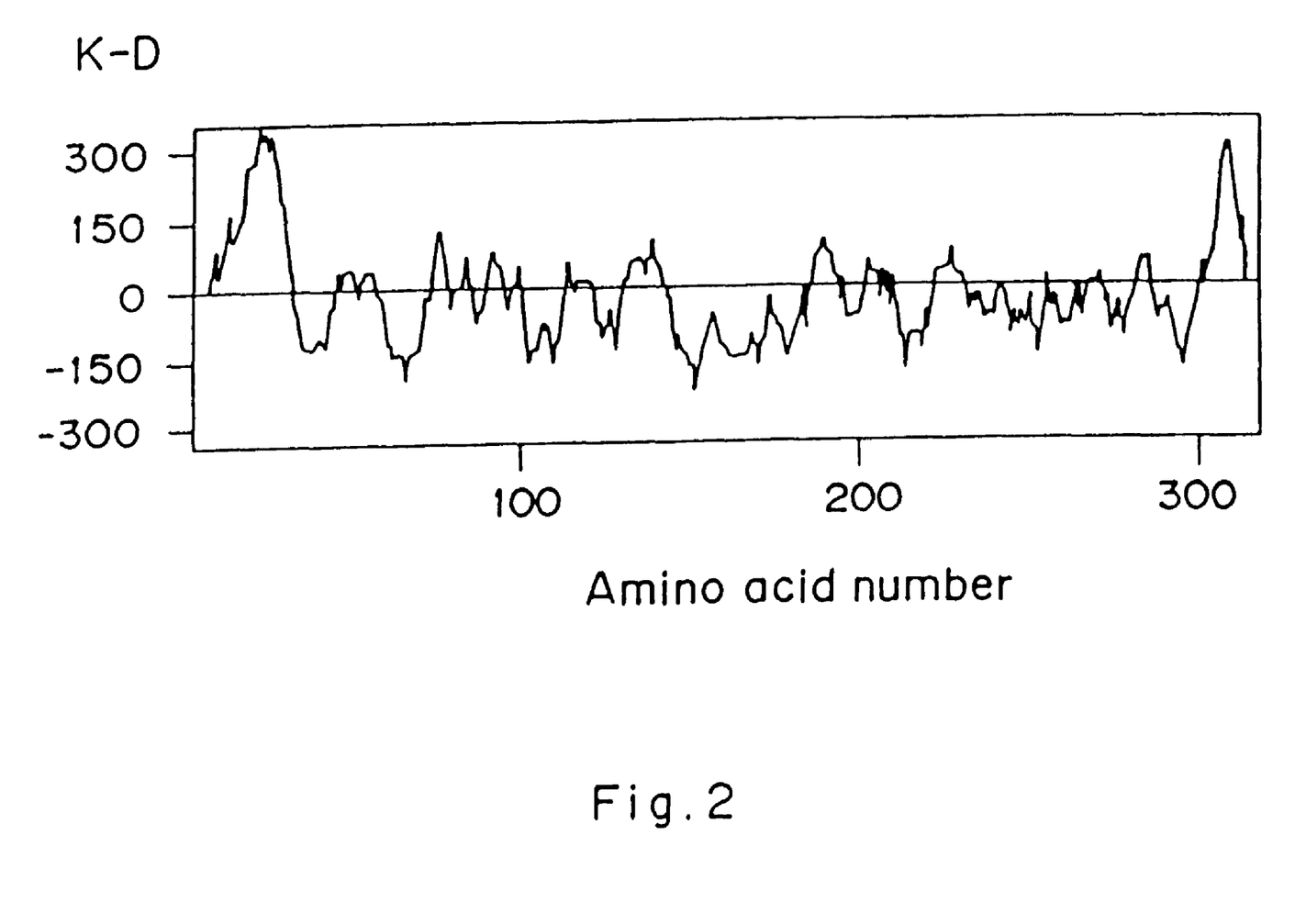
FIG. 2 shows the results of analyzing the hydrophobic region and the hydrophilic region of a gene obtained in Examples of the present invention.

The analysis of the hydrophobic region and the hydrophilic region of the gene obtained was performed by using a DNA analysis software Gene Works (FIG. 2). As a result, a hydrophobic region was recognized on the portion of 28 amino acid residues of the 1st to the 28th of sequence shown in the sequence No. 2 of the sequence table, and therefore it was presumed that the 29th amino acid glycine was the N terminal of mature protein.

Example 2

1. Construction of a Soluble Adhesion Molecule (sBst-1)

A soluble Bst-1 was constructed from a gene having a termination codon before the site corresponding to the 272$^{nd}$ amino acid of it according to a PCR-mutagenesis method [M. Kamman et al., Nucl. Acids Res., 15: 5404 (1989)]. Namely, it was produced according to the PCR-mutagenesis method using S1 and S2' (S1 primer: AAC CTC CAG AAG GAA AA (SEQ ID NO: 3); S2' primer: ACC CAA GCT TTC TAG ATC AAT AAA GAC TTG GGG (CTT (SEQ ID NO: 4) as primers and a plasmid pBst-1 as the template DNA.

100 μl of a PCR solution contains 10 mM of Tris-HCl (pH: 8.3), 50 mM of KCl, 0.25 mM of dNTP (dATP, dGTP, dCTP, dTTP), 1.5 mM of MgCl₂, 2.5 units of DNA polymerase AmpliTaq (manufactured by Perkin Elmer Cetus), 100 pmoles of each primer (S1 and S2') and 0.1 μg of a plasmid DNA. The PCR solution was covered with 50 μl of a mineral oil, heated at an initial temperature of 94° C. for 1.5 minutes, and after repeating a cycle of heating at 94° C. for 1 minute, at 50° C. for 1 minute and at 72° C. for 1 minute 25 times, it was subjected to incubation at 72° C. for 10 minutes.

The DNA fragment of 274 bp amplified according to the PCR method was purified with 1.5% low melting point agarose gel (FMC, manufactured by Bioproducts), and then digested with restriction enzymes BglII and HindIII (manufactured by Takara Shuzo). The obtained DNA fragment was ligated into the pBst-1 which was digested with restriction enzymes BglII and HindIII (manufactured by Takara Shuzo) by means of a DNA ligation kit (manufactured by Takara Shuzo) according to the procedure attached to the kit, digested with restriction enzymes EcoRI and HindIII, and then purified with 1.5% low melting point agarose gel (FMC, manufactured by Bioproducts) to obtain about 1.0 kb of the DNA fragment. At the terminals of the DNA fragment were made blunt ends with a Klenow fragment, and the DNA fragment was digested with a restriction enzyme BstXI, and then inserted into pEF-BOS having blunt end made by means of a Klenow fragment using a DNA ligation kit (manufactured by Takara Shuzo) according to the procedure attached to the kit to construct pΔ63-BOS.

2. Expression by a 293T Cell

The thus constructed expression plasmid pΔ63-BOS was transduced into *Escherichia coli* DH5α, and the obtained *Escherichia coli* was subjected to culturing to amplify the plasmid DNA in LB medium [Molecular Cloning: A Laboratory Manual, Sambrook et al., Cold Spring Harbor Laboratory Press (1989)] containing 50 μg/ml of ampicillin, and then the plasmid DNA was recovered from the *Escherichia coli* according to an alkaline method [Molecular Cloning: A Laboratory Manual, Sambrook et al., Cold Spring Harbor Laboratory Press (1989)]. The obtained plasmid DNA was subjected to purification by repeating ultra-centrifugation according to cesium chloride/ethidium bromide density-gradient twice, and then transfected into a 293T cell [cell line prepared by transfecting an SV40 large T antigen cDNA into a 293 cell (Transformed primary embryonal kidney, human ATCC CRL 1573)] according to a calcium phosphate method.

Namely, 10 μg of the purified plasmid DNA was dissolved into 100 μl of a buffer solution containing 1 mM of Tris-HCl and 0.1 mM of EDTA, and after 14 μl of 2M CaCl₂ was added therein, the resultant mixture was mixed with a buffer solution composed of 50 mM of HEPES (pH: 7.1), 280 mM of NaCl and 1.5 mM of sodium phosphate slowly, and then the obtained mixture was incubated at room temperature for 30 minutes, and added to 293T cells in a 10-centimeter culture dish. The 293T cells were cultured in DMEM (manufactured by GIBCO) medium containing 10% fetal calf serum (FCS, manufactured by Bioproducts) for 24 hours, and then moved into DMEM (manufactured by GIBCO) medium containing 1% fetal calf serum (manufactured by GIBCO) and cultured under the conditions of 37° C. and 5% CO₂.

The culture supernatant of the transduced 293T cells was recovered 48 hours after, concentrated to be 10-fold by means of a microconcentrator (Centoprep 10, manufactured by Amicon), and then used for the following test. In addition, pEF-BOS was similarly transfected into a 293T cell, and its culture supernatant was used as a control.

3. Growth Inhibition of a Pre-B Cell DW34 by sBst-1

The biological properties of sBst-1 were analyzed with the number of grown cells as an index using a mouse pre-B cell line DW34 growing dependent on stromal cells according to the following method.

First of all, the bone marrow stromal cell line RASV5-5 and the synovial cell line SynSV6-14 derived from patients with RA having pre-B cell growth-supporting ability were cultured in 24-well plates at a rate of 1×10⁵ cells per well, and 24 hours later radiation of 30 Gy was irradiated thereupon. The 2×10³ cells per well of the Pre-B cell line DW34 were added therein, and they were cultured in RPMI-1640 (manufactured by GIBCO) medium containing 10% FCS (manufactured by Bioproducts) under the conditions of 37° C. and 5% CO₂ for 4 days. The concentrated culture supernatant of 293T cells containing sBst-1 was added at the concentration shown in Table 1. The number of living cells of DW34 in each well was counted with trypan blue dye exclusion, and the growth-supporting ability of them was analyzed. As a result, the growth of DW34 was inhibited dependent on the concentration of the 293T cells containing sBst-1 in the culture supernatant as shown in Table 1.

TABLE 1

| Cell lines 293T cell containing sBst-1 (10-fold concentrated culture supernatant) % V/V | RASV5-5 | | SynSV6-14 | |
| --- | --- | --- | --- | --- |
| | sBst-1 added | Control | sBst-1 added | Control |
| 0 | 10.2 ± 1.4 | | 6.9 ± 0.1 | |
| 0.2 | 10.7 ± 1.6 | 10.4 ± 0.8 | 6.2 ± 0.2 | 7.2 ± 0.8 |
| 0.4 | 10.5 ± 1.6 | 11.1 ± 1.0 | 6.4 ± 0.9 | 6.4 ± 0.4 |
| 0.8 | 9.0 ± 2.2 | 12.1 ± 1.3 | 3.6 ± 0.2 | 8.7 ± 0.3 |
| 1.6 | 9.6 ± 0.2 | 11.6 ± 1.6 | 3.4 ± 0.7 | 6.6 ± 1.4 |
| 3.2 | 7.3 ± 0.8 | 11.2 ± 0.7 | 1.7 ± 0.3 | 4.3 ± 0.3 |

Number of DW34 cells per well
(RASV5-5: × 10⁻⁴, SynSV6-14: × 10⁻⁵) ± S.E.

Possibilities of Industrial Utilization

As described in detail above, the present invention relates to a gene encoding a polypeptide having pre-B cell growth-supporting ability, a vector containing said gene, transformants such as microorganisms or cells transformed by said vector, and a method for producing an adhesion molecule having pre-B cell growth-supporting ability using said gene, and therefore the gene of the present invention is capable of encoding the novel adhesion molecule enhancing the pre-B cell growth-supporting ability on the bone marrow cell and the synovial cell derived from patients with rheumatoid arthritis (RA) and multiple myeloma (MM).

According to the present invention, the homogeneous and purified adhesion molecule having pre-B cell growth-supporting ability can be produced in large quantities by inserting the gene of the present invention into a suitable vector, and then transforming ordinary host cells. Thus, according to the present invention, it becomes possible to identify multiple myeloma (MM) and rheumatoid arthritis (RA) and also prepare reagents for the clinical diagnosis thereof.

Although the foregoing invention has been described in some detail by examples for purposes of clarity of understanding, it will be obvious that certain changes and modifications may be practiced within scope of the appended claims.

What is claimed is:

1. A monoclonal antibody which binds to the polypeptide as set forth in SEQ ID NO: 1.

2. The monoclonal antibody of claim 1, wherein the monoclonal antibody is produced by the hybridoma having the accession number of FERM BP-4656 or FERM BP-4657.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 318 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO: 1:

```
Met Ala Ala Gln Gly Cys Ala Ala Ser Arg Leu Leu Gln Leu Leu Leu
                -25                 -20                 -15

Gln Leu Leu Leu Leu Leu Leu Leu Ala Ala Gly Gly Ala Arg Ala
            -10                  -5                   1

Arg Trp Arg Ala Glu Gly Thr Ser Ala His Leu Arg Asp Ile Phe Leu
 5                  10                  15                  20

Gly Arg Cys Ala Glu Tyr Arg Ala Leu Leu Ser Pro Glu Gln Arg Asn
                25                  30                  35

Lys Asn Cys Thr Ala Ile Trp Glu Ala Phe Lys Val Ala Leu Asp Lys
                40                  45                  50

Asp Pro Cys Ser Val Leu Pro Ser Asp Tyr Asp Leu Phe Ile Asn Leu
            55                  60                  65

Ser Arg His Ser Ile Pro Arg Asp Lys Ser Leu Phe Trp Glu Asn Ser
 70                  75                  80

His Leu Leu Val Asn Ser Phe Ala Asp Asn Thr Arg Arg Phe Met Pro
 85                  90                  95                 100

Leu Ser Asp Val Leu Tyr Gly Arg Val Ala Asp Phe Leu Ser Trp Cys
                105                 110                 115

Arg Gln Lys Asn Asp Ser Gly Leu Asp Tyr Gln Ser Cys Pro Thr Ser
                120                 125                 130

Glu Asp Cys Glu Asn Asn Pro Val Asp Ser Phe Trp Lys Arg Ala Ser
            135                 140                 145

Ile Gln Tyr Ser Lys Asp Ser Ser Gly Val Ile His Val Met Leu Asn
    150                 155                 160

Gly Ser Glu Pro Thr Gly Ala Tyr Pro Ile Lys Gly Phe Phe Ala Asp
165                 170                 175                 180

Tyr Glu Ile Pro Asn Leu Gln Lys Glu Lys Ile Thr Arg Ile Glu Ile
                185                 190                 195

Trp Val Met His Glu Ile Gly Gly Pro Asn Val Glu Ser Cys Gly Glu
            200                 205                 210

Gly Ser Met Lys Val Leu Glu Lys Arg Leu Lys Asp Met Gly Phe Gln
            215                 220                 225

Tyr Ser Cys Ile Asn Asp Tyr Arg Pro Val Lys Leu Leu Gln Cys Val
        230                 235                 240

Asp His Ser Thr His Pro Asp Cys Ala Leu Lys Ser Ala Ala Ala
245                 250                 255                 260

Thr Gln Arg Lys Ala Pro Ser Leu Tyr Thr Glu Gln Arg Ala Gly Leu
                265                 270                 275

Ile Ile Pro Leu Phe Leu Val Leu Ala Ser Arg Thr Gln Leu
                280                 285                 290
```

(2) INFORMATION FOR SEQ ID NO: 2:

(i) SEQUENCE CHARACTERISTICS:
        (A) LENGTH: 1411 base pairs
        (B) TYPE: nucleic acid
        (C) STRANDEDNESS: double
        (D) TOPOLOGY: linear     (ii) MOLECULE TYPE: cDNA to mRNA     (ix) FEATURE:
        (A) NAME/KEY: sig_peptide
        (B) LOCATION: 1..84
        (C) IDENTIFICATION METHOD: /note= "IDENTIFICATION METHOD: E"

(xi) SEQUENCE DESCRIPTION: SEQ ID NO: 2:

```
CGGGAAACGG CAAACAGCGA GATATCCGAG CGAGAGTCCC GCCCTGCATC AGTTTGCGGA      60
ACCGCCTTGG TAGAAGGAGA GAAGGGGAGT GGAGGAAGCA CGGGACTGGA GGGACCAAAG     120
TTCCCCGATG GCGGCCCAGG GGTGCGCGGC ATCGCGGCTG CTCCAGCTGC TGCTGCAGCT     180
TCTGCTTCTA CTGTTGCTGC TGGCGGCGGG CGGGGCGCGC GCGCGGTGGC GCGCGGAGGG     240
CACCAGCGCA CACTTGCGGG ACATCTTCCT GGGCCGCTGC GCCGAGTACC GCGCACTGCT     300
GAGTCCCGAG CAGCGGAACA AGAACTGCAC AGCCATCTGG GAAGCCTTTA AAGTGGCGCT     360
GGACAAGGAT CCCTGCTCCG TGCTGCCCTC AGACTATGAC CTTTTTATTA ACTTGTCCAG     420
GCACTCTATT CCCAGAGATA AGTCCCTGTT CTGGGAAAAT AGCCACCTCC TTGTTAACAG     480
CTTTGCAGAC AACACCCGTC GTTTTATGCC CCTGAGCGAT GTTCTGTATG CAGGGTTGC      540
AGATTTCTTG AGCTGGTGTC GACAGAAAAA TGACTCTGGA CTCGATTACC AATCCTGCCC     600
TACATCAGAA GACTGTGAAA ATAATCCTGT GGATTCCTTT TGGAAAAGGG CATCCATCCA     660
GTATTCCAAG GATAGTTCTG GGGTGATCCA CGTCATGCTG AATGGTTCAG AGCCAACAGG     720
AGCCTATCCC ATCAAAGGTT TTTTTGCAGA TTATGAAATT CCAAACCTCC AGAAGGAAAA     780
AATTACACGA ATCGAGATCT GGGTTATGCA TGAAATTGGG GGACCCAATG TGGAATCCTG     840
CGGGGAAGGC AGCATGAAAG TCCTGGAAAA GAGGCTGAAG GACATGGGGT TCCAGTACAG     900
CTGTATTAAT GATTACCGAC CAGTGAAGCT CTTACAGTGC GTGGACCACA GCACCCATCC     960
TGACTGTGCC TTAAAGTCGG CAGCAGCCGC TACTCAAAGA AAAGCCCCAA GTCTTTATAC    1020
AGAACAAAGG GCGGGTCTTA TCATTCCCCT CTTTCTGGTG CTGGCTTCCC GGACTCAACT    1080
GTAACTGGAA ACTGTGTTGC TCTAACCCTC CTCCAGCCCT GCAGCCTCCC CTTGCAGTCA    1140
TCATTCGTGT TCTGTGTATA CCAAATGATT CTGTTATCTA AAGAAGCTTT TTGCTGGGAA    1200
AACGATGTCC TGAAAATGGT ATTTCAATGA GGCATATGTT CAGGATTTCA GAAACAAGAA    1260
GTTAGTTCTA TTTAGCAGGT TAAAAAATGC TGCATTAGAA TTAAAGCAAG TTATTTTCTT    1320
ATTTGTATAA TGACACAAAG CATTGGGAGT CAGACTGCTT GTATATTATC AAACATTTTA    1380
AGAGAATTCT AATAAAGCTG TATTTTACAT C                                   1411
```

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (ii) MOLECULE TYPE: oligonucleotide primer     (xi) SEQUENCE DESCRIPTION: SEQ ID NO: 3:

```
AACCTCCAGA AGGAAAA                                                      17

(2) INFORMATION FOR SEQ ID NO: 4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO: 4:

AACCAAGCTT TCTAGATCAA TAAAGACTTG GGGCTT                                 36
```